United States Patent [19]

Davis et al.

[11] Patent Number: 5,391,480
[45] Date of Patent: Feb. 21, 1995

[54] METHOD FOR DETECTING A NUCLEOTIDE AT A SPECIFIC LOCATION WITHIN A NUCLEIC ACID USING EXONUCLEASE ACTIVITY

[75] Inventors: Ronald W. Davis, Palo Alto, Calif.; Arthur Myles, Hopedale, Mass.

[73] Assignee: Collaborative Research, Inc., Waltham, Mass.

[21] Appl. No.: 803,683

[22] Filed: Dec. 3, 1991

Related U.S. Application Data

[63] Continuation of Ser. No. 352,956, May 17, 1989, abandoned, which is a continuation-in-part of Ser. No. 326,537, Mar. 21, 1989, abandoned.

[51] Int. Cl.⁶ ............................................. C12Q 1/68
[52] U.S. Cl. ........................................ 435/6; 435/91.1; 435/91.2; 435/808; 436/501; 536/22.1; 536/23.1; 536/24.31; 536/24.32; 536/24.33; 935/78; 935/88
[58] Field of Search ............ 435/6, 91, 808, 91.1, 435/91.2; 436/501; 536/27-29, 22.1, 23.1, 24.31-24.33; 935/17, 78, 88

[56] References Cited

U.S. PATENT DOCUMENTS

| 4,656,127 | 4/1987 | Mundy ........................ 435/6 |
| 4,851,331 | 7/1989 | Vary et al. ................. 435/6 |

OTHER PUBLICATIONS

Petruska et al. (1988) Proc. Natl Acad Sci (USA) vol. 85, pp. 6252–6256.
Brutlag et al. (1972) J. Biol. Chem., vol. 247, No. 1, pp. 241–248.
Saiki et al. (1986) Nature, vol. 324, pp. 163–166.
Amselen et al. (1988) Am. J. Hum. Genet., vol. 43, pp. 95–100.
Saiki et al. (1988) The New England J. of Med., vol. 319, No. 9, pp. 537–541.
Saiki et al. (1988) Abstract 0377 of the Annual Meeting of the Am. Soc. of Hum. Genet., 13.2.
Matthews et al. (1988) Anal. Biochem. vol. 169, pp. 1–25.

*Primary Examiner*—Margaret Parr
*Assistant Examiner*—Ardin H. Marschel
*Attorney, Agent, or Firm*—Wolf, Greenfield & Sacks

[57] ABSTRACT

A novel technique for determining the existence or nonexistence of a test nucleotide on a strand of DNA is provided. The determination advantageously uses an exonucleolytic agent that is capable of retaining a labeled nucleotide in a primer if there is a match between the test nucleotide on the strand of DNA and the complementary nucleotide on the primer, but not if there is a mismatch. The presence or absence of the test nucleotide then may be established by determining whether the label is preserved or lost following the reaction.

13 Claims, 3 Drawing Sheets

METHOD FOR DETECTING A NUCLEOTIDE AT A SPECIFIC LOCATION WITHIN A NUCLEIC ACID USING EXONUCLEASE ACTIVITY

This application is a continuation of application Ser. No. 07/352,956, now abandoned, filed May 17, 1989, which is a continuation in-part of application Ser. No. 07/326,537, filed Mar. 21, 1989, now abandoned, and entitled MULTIPLEX DNA DIAGNOSTIC TEST.

This invention relates to methods and products useful for detecting the presence or absence of a particular nucleotide at a specific location on a strand of DNA. By using the methods and products of this invention, it is possible to determine the genotype of an individual at any locus of interest.

A single nucleotide position on a strand of DNA may be responsible for polymorphism or allelic variation. There are known disease states that are caused by such variation at a single nucleotide position. The usefulness of detecting such variation includes but is not limited to gene typing, karyotyping, genotyping, DNA family planning, diagnostics (including infectious disease), prenatal testing, determining parentage, and forensic analysis.

The typical methods for determining such variation have been to hybridize specific probes to permit Southern Blots containing different DNA digests to test for variation in the length of specific restriction fragments, or to amplify specific regions of DNA samples by polymerase chain reaction (PCR), and test for nucleotide variation by sequence analysis or by hybridization with allele specific probes.

Each of these methods has certain drawbacks, including: the lack of reproducibility of Southern analysis, the need for running gels to separate DNA fragments, and the extended amount of time required to complete the necessary steps in the process. PCR techniques suffer from occurrence of false signals arising from contamination, and the time and technical expertise required for the determination of sequences from PCR amplified samples. However, perhaps the most serious drawback is that both methods require a number of separate analyses to test for variation at more than one DNA locus.

SUMMARY OF THE INVENTION

The present invention involves a novel technique for determining the existence or nonexistence of a particular nucleotide at a particular position on a strand of DNA. The determination requires the use of a special primer capable of pairing with the strand of DNA and carrying a detectable label which will be retained if there is a base pair match at the nucleotide of interest (i.e., the test nucleotide), but will be lost if there is a mismatch at the nucleotide of interest. The determination advantageously employs an exonucleolytic agent that will remove the label if there is a base pair mismatch at the nucleotide of interest when the labeled primer and DNA are paired with one another.

According to one aspect of the invention, a test sample of DNA is treated with a labeled oligonucleotide primer of the invention, the primer being capable of pairing with a first portion of the DNA adjacent to the test nucleotide. The primer of the invention includes a labeled nucleotide at or near the position opposite to the test nucleotide when the primer and the DNA are paired. Then, the primer-DNA pair is subjected to conditions that allow retention of the labeled nucleotide attached to the primer if there is a base-pair match at the test nucleotide position, but not if there is a mismatch. Then, the presence or absence of the label on either the excised free base or on the extended primer is determined.

The method of the invention employs an agent which is capable of excising the label in the primer if there is a base pair mismatch at the nucleotide of interest when the primer and DNA are paired with one another. The agent preferably also includes polymerase activity as well as exonuclease activity, although polymerase activity is nonessential. The important consideration is that conditions be applied to the paired primer-DNA strand such that the label in the primer will be retained in the presence of a base pair match at the test position, but not in the presence of a base pair mismatch at the test position.

The invention has the advantage of not requiring the time-consuming and troublesome gels employed in certain of the prior art detection techniques.

The presence or absence of retained label attached to the primer may be detected in various ways. For example, loss of label from the primer could be measured by detecting the presence of label unassociated with the primer. Any free label could be separated from the larger primers and sample DNA molecules by methods such as ultrafiltration, gel filtration, HPLC, mass spectrometry or capillary zone electrophoresis. Detection of the presence of free label would indicate that a mismatch had occurred in the test and that the exonucleolytic agent had removed the label from the primer.

Alternatively, the primers may be extended by the action of a polymerase in the presence of an exonucleolytic agent. A match or mismatch then may be detected by determining the presence or absence of label on the extension product. Such a determination is well within the knowledge of one of ordinary skill in the art, and may be accomplished, for example, by hybridizing the extension product to its complement fixed to a solid support and determining the presence or absence of label.

In another approach, the presence or absence of label in the primer extension product is determined according to a method that requires an oligonucleotide primer having attached to it a unique tail sequence non-complementary with the DNA. The primer extension product then is applied to a substrate carrying an oligonucleotide, at least in part complementary to the unique tail sequence, of the extension product, under conditions that allow the unique tail sequence to hybridize to the complementary oligonucleotide on the substrate. Preferably, both the tail and the oligonucleotide complementary to the tail are comprised of repeating units of complementarity. This favorably affects the kinetics of hybridization, increasing the speed and the sensitivity of the test. Of course, unreacted primer must be minimized or removed prior to the assay phase of this approach to prevent it from hybridizing to the substrate and interfering with The interpretation of the results.

In still another approach, the presence or absence of the mismatch may be determined in solution or on a solid support by using nonradiative fluorescent resonance energy transfer (FRET, see Cardullo et al., 1988, *Proc. Nat'l. Acad. Sci. USA* 85: 8790–8794) between two suitable fluorescent labels. With this technique, the labels would allow effective FRET only if both fluorescent labels were maintained in close proximity. In this approach, two labels could either be provided in adjacent positions on the primer, or one could be on the primer and the other incorporated via intercalation into the duplex DNA formed by the primer and the test DNA strand. A mismatch would interfere with measurable FRET by allowing exonucleolytic excision of one or both of the fluorescent labels.

The invention allows for determining genotype at desired genetic loci. The test DNA is exposed to a plurality of different oligonucleotide primers, each of the primers being complementary to a genetic locus of interest. Each primer carries a labeled nucleotide at or near one end, said labeled nucleotide also being at or near the position opposite the test nucleotide (which is known to vary in different alleles of the locus) when the primer and test DNA are paired. The treatment includes subjecting the primers and DNA to conditions that allow the primers and DNA to pair. The paired primer-DNA then is treated with an exonucleolytic agent under conditions that allow the retention of label in the primer if there is a match between any test nucleotide and the complementary nucleotide on the primer opposite to a test nucleotide, but loss of the label in the primer if there is a mismatch. The presence or absence of label in a primer (which corresponds to the presence or absence of an allelic complementation) then may be determined by applying the samples containing the reaction products, after denaturation, to substrates spotted at distinct locations with unique oligonucleotides complementary to the polymerase/exonuclease-catalyzed extension products. If label has been retained in the primer extension product, then it will be detected at a unique location on the substrate; the product attaches to the substrate at only one location via the hybridization to the unique, complementary oligonucleotide found only at that location. The presence or absence of a specific allelic sequence thus may be determined by detecting the presence or absence of label at a specific location on the substrate, The foregoing test for genotype is particularly useful when determining genotype for a single allele. For identification of multiple alleles, the technique may be repeated using allele-specific primers on multiple samples. Alternatively, multiple alleles may be assayed simultaneously using primers of different allelic complementarity having allele-specific labels or tails.

The invention thus provides an oligonucleotide primer having a sequence of nucleotides complementary with at least a portion of a DNA strand and terminating at or very close to a test nucleotide position on the DNA strand, nucleotide variation at that test position being responsible for polymorphism. The oligonucleotide primer has a labeled nucleotide at or near the position which will be opposite the test nucleotide when the primer and the test DNA are hybridized. Sets of such oligonucleotide primers are provided for determining the genotype of an individual at specific loci.

The invention further utilizes an agent with exonucleolytic activity capable of excising the label on the primer of a paired primer-DNA strand having a mismatched base-pair at or close to an end of said primer. This exonucleolytic agent may have no polymerase activity. The exonucleolytic agent may be a native exonuclease or polymerase with exonucleolytic activity, a mutant exonuclease or polymerase with exonucleolytic activity, or a non-mutant exonuclease or polymerase with exonucleolytic activity treated to impart the necessary properties.

The invention also provides a substrate having attached to it at one location a first oligonucleotide having a first sequence and at a second location a second oligonucleotide having a sequence different from and non-complementary with the first oligonucleotide. These substrate oligonucleotides are complementary with the primers, their tails, or their extension products. Preferably, the substrate is spotted with oligonucleotides firmly bound to the substrate but accessible for hybridization with complementary sequences. The substrate may have attached to it in such a manner at known locations many different oligonucleotides which are non-complementary with each other.

The products of the invention may be advantageously provided in kits. The kits may include a plurality of different oligonucleotide primers and a plurality of oligonucleotides complementary to portions of DNA extended by the action of the polymerase/exonuclease of the invention on the primers when paired to the test DNA. Most preferably, the kit includes a substrate having attached at different locations the complementary oligonucleotides.

DETAILED DESCRIPTION OF THE DRAWINGS

Figure 1:
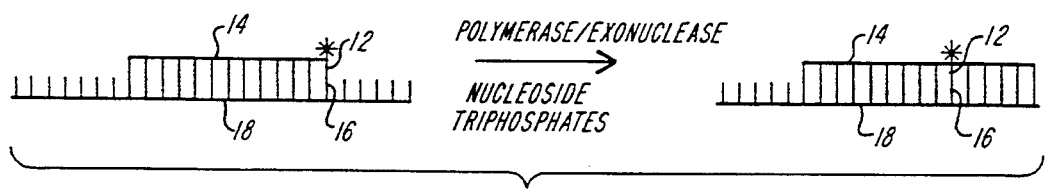
FIG. 1 schematically shows the synthesis of an extension product with retention of label obtained by using the exonuclease/polymerase of the invention when there is a match at the test position.

The present invention involves a novel technique for determining the existence or nonexistence of a particular nucleotide at a specific locus on a strand of DNA, at least a portion of which strand has a known sequence, adjacent to and including the locus of interest. The invention may be used in connection with many medical tests, including all of those listed in the background of the invention. It is particularly useful in determining an individual's genotype at the test locus, especially as the genotype relates to the existence of an allele or mutation responsible for a disease state or as it relates to an individual's identity.

The invention involves using a labeled oligonucleotide primer that will either create a base pair match or mismatch between a test nucleotide on the DNA strand and the labeled nucleotide at the opposite position on the primer when the primer is paired with the DNA strand. The primer is labeled at only one or at a few position(s), that are near or at the position opposite the test nucleotide. First, the primer and DNA strand are caused to pair. Then, conditions are applied to the primer-DNA pair that will cause retention of the label in the primer product in the presence of a match, but not in the presence of a mismatch. The test involves the use of an exonucleolytic agent that removes the label on the primer if there is a mismatch when the primer and DNA are paired, but does not remove the label on the primer if there is a match.

The term "oligonucleotide" as used herein in referring to primers, extension products, tails and products complementary to primers, extension products and tails, refers to a molecule comprised of two or preferably more than three deoxyribonucleotides or ribonucleotides, synthetic or natural. The exact size of the molecule may vary according to its particular application.

The term "primer" as used herein refers to an oligonucleotide which, when paired with a strand of DNA, is capable of initiating the synthesis of an extension product in the presence of a suitable polymerization agent. Preferably, the primer is an oligoribonucleotide and most preferably is an oligodeoxyribonucleotide. The primer, however, may be other than a ribonucleotide. The primer must be sufficiently long to hybridize uniquely to the test region of the test DNA strand, and the primer must contain a labeled nucleotide at or near the position opposite the test nucleotide of the test DNA strand. The exact length of the primer will depend on many factors, including the degree of specificity of pairing required, and the temperature and ionic strength during hybridization.

The term "exonucleolytic agent" as used herein may be any compound or system which will function to accomplish the removal of the label when the appropriate nucleotide(s) are mismatched. Suitable enzymes for this purpose may include DNA polymerases with exonucleolytic acitivity, single-strand specific exonucleases, and other enzymes, including heat-stable enzymes. Generally, the exonucleolytic agent will be a 3' to 5' exonuclease directed to the 3' end of each primer. There are also agents, however, which remove nucleotides at the 5' end or both from the 5' and the 3' end, and these may also be used.

The term "terminal nucleotide" as used herein in referring to oligonucleotide primers refers to the terminal nucleotide at either end of the primer. When the primer is hybridized to the test DNA, the nucleotide position opposite to the position of the test nucleotide on the DNA strand is located at or close to a terminal nucleotide.

The term "pairing" as used herein contemplates any and all methods of sequence specific pairing between the primer and a strand of DNA including the pairing of a primer with double stranded DNA, so long as an exonucleolytic agent may act on the product of such a pairing. Typically, however, a single stranded primer and a single strand of DNA will be paired by subjecting them to conditions which cause them to hybridize to one another. The primers are selected to be "substantially" complementary to the strands of each specific DNA sequence being tested. By substantially it is meant that the primer is sufficiently complementary to pair with the test DNA. The primer sequence then need not reflect the exact sequence of the test DNA. However, in a preferred embodiment, the primer is at least 20 nucleotides long and contains no mismatches with the complementary DNA strand except in certain instances at or close to the nucleotide position complementary to the test nucleotide.

The term "label" as used herein refers to, but is not limited to, the following classes of reporter groups. Primary labels such as radioisotopes and fluorescent groups are signal generating reporter groups which can be detected without further modifications. Secondary labels such as biotin and various protein antigens act as "bridges" and require the presence of a second intermediate for production of a detectable signal. For biotin, the secondary intermediate may include. streptavidin-enzyme conjugates. For antigen labels, secondary intermediates may include antibody-enzyme conjugates. Some fluorescent groups act as secondary labels because they transfer energy to another group in the process of nonradiative fluorescent resonance energy transfer, and the second group produces the detected signal.

The terms "match" and "mismatch" refer to the hybridization potential of paired nucleotides in complementary strands of DNA. Matched nucleotides hybridize efficiently, such as the classical A-T and G-C base pairs. Mismatches are other combinations of nucleotides which do not hybridize efficiently.

Precursors to the labeled oligonucleotide primers (including tails) of the invention or the oligonucleotide primers themselves may be prepared using any suitable method, such as, for example, methods using phosphotriesters and phosphodiesters well known to those skilled in the art. In one such automated embodiment, diethylphosphoramidites are used as starting materials and may be used for synthesis of oligonucleotides as described by Beaucage and Caruthers, 1981, Tetrahedron Letters, 22: 1859–1862. One method for synthesizing oligonucleotides on a modified solid support is described in U.S. Pat. Nos. 4,458,066 and 4,500,707. It is also possible to use a precursor primer or primer which has been isolated from a biological source (such as a restriction endonuclease digest of plasmid or phage DNA).

Labels may be applied to precursor primers by any suitable method including enzymatic methods. For example, DNA polymerases such as the Klenow fragment of DNA polymerase I will add certain labeled nucleotides to the 3' end of a precursor primer in the presence of the suitable template DNA strand. Suitable labels include, but are not limited to, $^{32}P$, biotin, and fluorescent moieties such as rhodamine or fluorescein.

According to a preferred embodiment of this invention, an agent for polymerization having exonuclease activity is used to indicate whether a primer contains a nucleotide which is complementary to, or not complementary to, the test nucleotide in the DNA strand. Typically, a single stranded primer when hybridized to a longer single strand of DNA in the presence of nucleoside triphosphates and an agent for polymerization, at suitable temperature and pH, will allow the synthesis of an oligonucleotide attached to and extending from the primer, the oligonucleotide being complementary with the single strand of DNA. Many known agents of polymerization will not catalyze extension of a primer from a mismatched terminal base pair. Rather, the agent of polymerization will excise the mismatched base pair by its exonucleolytic activity and then initiate the synthesis of an extension product from a matched pair.

Figure 2:
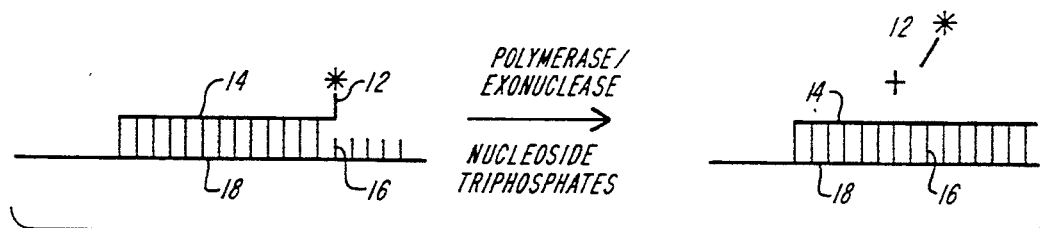
FIG. 2 schematically illustrates the synthesis of an extension product with loss of label obtained by using the exonuclease/polymerase of the invention when there is a mismatch at the test position.

As shown in FIG. 1, if there is complementary base pairing (a match) between the labeled terminal nucleotide 12 of the primer 14 and the test nucleotide 16 on the test DNA 18, an extension product will be synthesized and the labeled nucleotide (*) will be retained. However, as shown in FIG. 2, if there is a mismatch between the labeled terminal nucleotide 12 of the primer 14 and the test nucleotide 16, then an extension product will be synthesized but only after excision of the mismatched labeled nucleotide opposite the test position in the DNA strand.

The synthesis of the extension product may be according to methods well-known to those skilled in the art. For example, if a deoxyribonucleotide extension product is being synthesized, the hybridized primer-DNA strand must be treated with a polymerase having exonucleolytic activity in the presence of deoxyribonucleoside triphosphates (dATP, dCTP, dGTP, dTTP). According to a preferred embodiment, the primer carries a labeled nucleotide at or close to its 3' end. Typical labels include $^{32}$P-labeled, biotin labeled, or fluorescent labeled nucleoside triphosphates. The labelled nucleotide is at or near the position opposite the test position on the test DNA strand when the primer is hybridized to the test DNA strand.

By using a polymerase/exonuclease, which excises a mismatched nucleotide in the primer before synthesizing an extension product, and by subjecting the hybridized primer-DNA to conditions that permit excision and extension, the presence or absence of a specific nucleotide on a strand of DNA may be determined. For example, assume that a gene for a health trait includes the following known sequence: 3'GATCGAATTG-GCACACGTT5'. Also assume the gene for the disease state is due to or correlated with a substitution at a single test nucleotide position, underlined: 3'GATC-GAATTGGCCCACGTT5'. A primer that could be used to detect the presence or absence of the disease state then would be: 5'CTAGCTTAACCGG*3', in which the terminal "G" is labeled (the * denotes the label). This primer is capable of hybridizing with either of the foregoing DNA sequences. However, when the primer hybridizes to the DNA sequence characteristic of the healthy state, there will be a mismatch at the terminal end of the primer, an A being paired with a G. If that hybridized primer-DNA strand is treated with a polymerase/exonuclease then an extension product will be formed, but only after excision of the labeled "G" residue of the primer. On the other hand, when the primer is hybridized with the DNA sequence characteristic of the disease state, there is a match between the terminal nucleotide of the primer and the test nucleotide on the DNA strand (G-C). That hybridized primer-DNA strand will initiate the synthesis of an extension product with retention of the labeled "G" residue in the presence of the polymerase/exonuclease of the invention.

To determine whether a sample of test DNA carries the DNA characteristic of the healthy state or the disease state, the labeled primer is added to a sample of test DNA under conditions allowing the primer to hybridize to the test DNA. A polymerase/exonuclease and nucleoside triphosphates then are added and the mixture is subjected to conditions that allow excision and synthesis of an extension product. It then is determined whether label is present or absent in the resulting extension product. If label was retained in the extension product, then there was a match indicating the presence of the DNA characteristic of the disease state. If label was lost in the extension product, then there was not a match and the nonexistence of the DNA characteristic of the disease state is established.

Detection methods well known to those skilled in the art may be employed to determine the presence or absence of label in the extension product. DNA complementary to the extension product may be attached to a substrate such as filter paper or a nylon membrane. This substrate may be treated with the products of the test reaction under conditions that would allow any extension product to hybridize to the complementary DNA on the substrate. The substrate then would be tested for the presence or absence of any label attached via hybridization to the complementary strand. If there is label on the substrate, then the label was retained during synthesis of the extension product. If there is no label on the substrate, then the label was excised prior to synthesis of the extension product.

Figure 3:
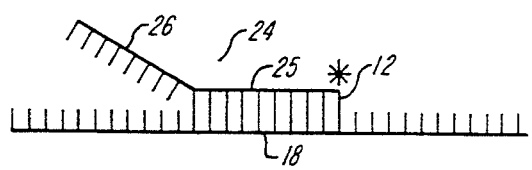
FIG. 3 schematically shows an oligonucleotide of one embodiment of the invention, which primer includes a unique tail sequence.
Figure 4:
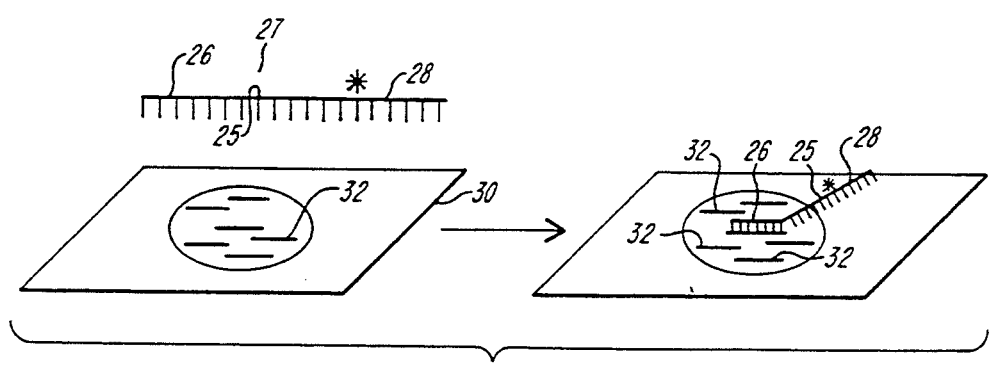
FIG. 4 schematically shows the detection of an extension product formed with retention of label on the oligonucleotide primer of FIG. 3.

According to another embodiment of the invention, the test is improved by using a primer 24 having primer portion 25 and a tail portion 26 attached to and extending from the end of the primer portion 25 opposite the labeled terminal nucleotide 12. Preferably, the tail portion 26 is unique and is non-complementary with the test DNA. Such a primer is shown schematically in FIG. 3 hybridized to a longer strand of DNA 18. When using the labeled primer 24 of the invention and a polymerase/exonuclease, an extension product 27, having three portions, is formed (FIG. 4). The extension product will include the extension portion 28, the primer portion 25, labeled or unlabeled depending on the test nucleotide, and the tail portion 26.

Improvements to the speed and sensitivity of the assay are achieved using such primers having tails. The presence or absence of label in the primer portion of the extension product may be detected by using substrates such as filter paper 30 spotted with a great excess of oligonucleotide complementary to the tail portion 26. Because such complementary oligonucleotide DNA 32 may be synthesized inexpensively in great quantity and therefore may be applied to the substrate in great excess (FIG. 4), the rate and amount of hybridization between the tail portion 26 of the extension product 27 and the complementary oligonucleotide 32 on the substrate is enhanced.

Most preferably, the oligonucleotide of the tail and the oligonucleotide complementary to the tail both consist of repeating units of complementation. Most preferably, the tail portion 26 is a polymer consisting of repeating units of an oligonucleotide 14 nucleotides long, and the complementary oligonucleotide 32 is a polymer consisting of repeating units of an oligonucleotide that is also 14 nucleotides long. The use of such repeating units of complementation favorably affects the kinetics of hybridization, further increasing the speed and the sensitivity of the assay.

Figure 5:
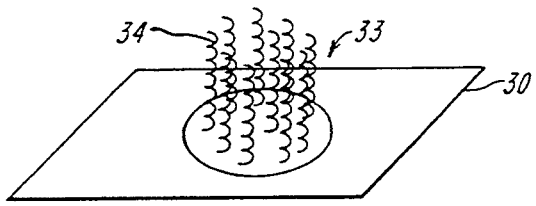
FIG. 5 schematically shows a detection substrate for detecting the label on the oligonucleotide primer of FIG. 3.

A substrate having attached to it a plurality of polymers 33 of such repeating units 34 of complementation is shown schematically in FIG. 5. Preferably, the plurality of polymers 33 are covalently linked to the substrate at a very high concentration to form a solid solution that presents a great many available hybridization sites, unobstructed by the substrate to which the polymers are attached. These substrates with attached polymers may be dried out and stored for considerable periods.

The products and methods of the invention may be used advantageously to determine allelic variation in genotyping studies. For example, if allelic variation is due to a single nucleotide substitution (or is correlated with such a substitution), then test DNA can be treated using primers for both alleles to determine whether an individual is homozygous or heterozygous with respect to those alleles. Such a test is performed advantageously using primers for each allele having tails differing from one another so that only a single test carried out in a single vessel is necessary.

Figure 6:
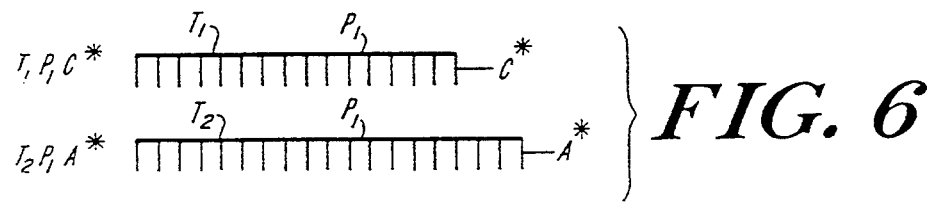
FIG. 6 schematically shows a set of preferred oligonucleotide primers.

To accomplish this, two primers are constructed as shown in FIG. 6. Each primer has a primer portion P that is complementary to the same DNA, except that the labeled terminal nucleotide on each of the primers is different. The labeled terminal nucleotide on one of the primers is complementary to the nucleotide determining one allele and the labeled terminal nucleotide on the other primer is complementary to the nucleotide determining the second allele. In the example shown, the labelled terminal nucleotides are cytosine and adenosine (C and A, respectively).

At the opposite end of each of the primers is attached a unique tail. By "unique" it is meant that a sequence complementary to one tail will not hybridize with the other tail. Moreover, neither of the tails and neither sequence complementary to the tails should be capable of hybridizing with the test DNA. It is believed that a single nucleotide substitution on an oligonucleotide 14 nucleotides long is sufficient to prevent cross hybridization. Preferably there are at least two nucleotide substitutions to distinguish each tail. As is understood by those skilled in the art, the synthesis of a set of thousands of such unique tails 14 nucleotides long is possible.

The designations for the primers shown in FIG. 6 are $T_1P_1C^*$ and $T_2P_1A^*$: the T signifying tail and the subdesignation signifying the sequence of the tail; the P signifying primer portion and the subdesignation signifying the sequence of the primer; and the last letter signifying the labeled terminal nucleotide. Thus, $T_1P_1C^*$ stands for tail sequence number 1, primer sequence number 1, and a cytosine terminal nucleotide. $T_3P_2A^*$ would stand for tail sequence number 3, primer sequence number 2 and adenosine as a terminal nucleotide.

Figure 7:
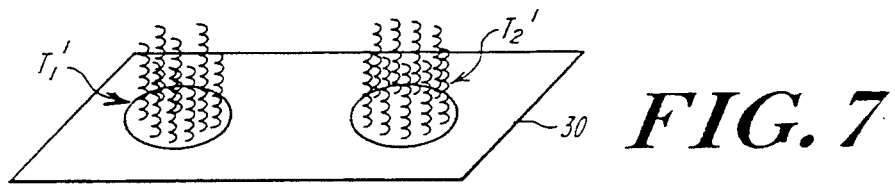
FIG. 7 schematically shows a substrate for determining allelic variation.

The primers shown in FIG. 6 ($T_1P_1C^*$ and $T_2P_1A^*$) are added to test DNA under conditions that allow the primers to hybridize with the test DNA. Then the hybridized primer-DNA may be treated with a polymerase/exonuclease and nucleoside triphosphates under conditions that allow the synthesis of an extension product with retention of label if there is a match at the labeled terminal nucleotide. Thus, if the test DNA has a G at the test nucleotide, which is complementary to the labelled terminal nucleotide of the primer $T_1P_1C^*$, then there is a match and an extension product will be synthesized with retention of the label. Likewise, if the test DNA has a T at the test nucleotide which is complementary to the terminal nucleotide of the primer $T_2P_1A^*$, then there is a match and an extension product will be synthesized, with retention of the label. The sample containing the extension products then is applied to a substrate having spotted at different locations an oligonucleotide complementary to tail number 1 ($T_1'$) and an oligonucleotide complementary to tail number 2 ($T_2'$) (FIG. 7). Extension product will hybridize at $T_1'$ via hybridization of tail number 1 to the $T_1'$ oligonucleotide and extension product also will hybridize to spot $T_2'$ via hybridization of tail number 2 to the oligonucleotide at $T_2'$. The presence of label at both locations would indicate a heterozygous individual. If, on the other hand, label is detected only at spot $T_1'$, then the individual carries only a G at the test nucleotide. Likewise, if label is only detected at spot $T_2'$, then the individual carries only a T at the test nucleotide position. Thus, the genotype of an individual at a single locus may be determined in a single test, two alleles being tested for simultaneously.

Figure 8:
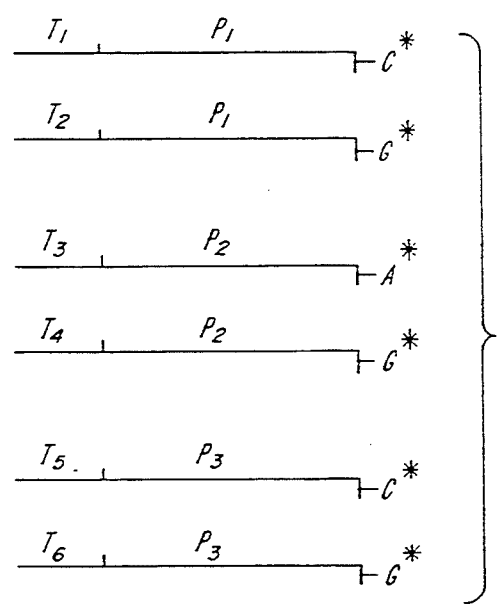
FIG. 8 schematically shows a second set of oligonucleotide primers for detecting multiple alleles at multiple loci.

It will be understood by those skilled in the art that the genotype could have been tested by using primers having the same tail, rather than unique tails. To accomplish this, the primers must be tested separately with separate samples of test DNA. It, however, is an advantage of the invention that by using unique tails, any number of alleles or loci may be tested for simultaneously. Thus, tests for different genes and tests for multiple alleles on different genes may be accomplished simultaneously according to the invention. For example, a plurality of primers may be constructed, including primers complementary to different genes. FIG. 8 depicts a set of primers for three genes, each gene having two alleles. $T_1P_1C^*$ and $T_2P_1G^*$ are complementary to the same gene, but to different alleles; $T_3P_2A^*$ and $T_4P_2G^*$ are complementary to the same second gene, but to different alleles; and $T_5P_3C^*$ and $T_6P_3G^*$ are complementary to a third gene, but also to different alleles of that gene. Each of the primers has a unique tail ($T_1$, $T_2$, $T_3$, $T_4$, $T_5$, and $T_6$), and the terminal nuclotide of each primer is labelled. When this set of primers is mixed with a single sample of test DNA, only those primers that have hybridized to the test DNA and have matching nucleotides at the terminal end of the primer are capable of initiating the synthesis of an extension product retaining the labeled nucleotide. After the conditions for the exonuclease/polymerase reaction have been applied, the label on any unreacted primers may be removed by use of a potent 3' to 5' exonuclease activity such as that of T4 DNA polymerase, which prefers single-stranded DNA. Alternativly, label on any unreacted primers may be removed by separating extension products from unreacted primers. Next, the products of the reaction may be placed in contact with specific oligonucleotides, complementary to the unique tails, spotted at different locations on a substrate. Then, the existence of label on the reacted primers is determined by looking for the presence of label on the substrate, potentially present due to reacted primers hybridizing via their tails to the substrate. The existence of label at a particular location on the substrate indicates that label was retained on the primer portion of an extension product, the primer being identified by its unique tail complementary only with the oligonucleotide at the particular location. Thus, the presence or absence of each of the various genes and multiple alleles may be tested simultaneously using a single sample of test DNA.

For the implementation of these first two embodiments, the complementary DNA attached to the substrate may be complementary to at least one of the following: a portion of the primer (including complementation to only the tail portion), a portion of the synthesized extension product, or a portion of both. If the complementary DNA on the substrate is complementary to a portion of the primer, it would be necessary to remove nonhybridized, labelled primers from the reaction mixture prior to contact of the mixture with the substrate-bound oligonucleotides. Otherwise, the presence of label on the substrate might not be the result of a match between the labeled nucleotide and the test nucleotide, but might simply result from the presence of primer which failed to hybridize. This could be accomplished in a variety of ways including: ensuring that most of the labelled primer molecules had an opportunity to hybridize to the test DNA and undergo reaction with a polymerase/exonuclease; treating the unreacted primers with a potent exonuclease preferring single stranded DNA to excise the labelled terminal nucleotide; or alternatively, removing unreacted primer molecules from the solution containing the extension product.

In order to ensure that most of the labeled primers participate in the reaction of the invention, it is helpful to repeat the primer annealing and exonucleolytic phases of the reaction several times. For example, the reaction may be heated to dissociate hybridized extended primer and test DNA and then cooled to permit annealing of new primers to the test DNA. If the polymerase/exonuclease used is not heat stable, then more would be added, and the reaction mixture incubated under conditions to permit exonucleolytic action and polymerization. The entire cycle is repeated until calculations indicate that most of the added labeled primer had participated in the reaction. Alternatively, a control primer is included in a separate similar reaction. The control primer carries a labeled terminal nucleotide which is not complementary to the corresponding nucleotide in any of the alleles in question. Loss of most of the label in the control reaction indicates that sufficient cycles were carried out to permit most of the added labeled primers to participate in the reaction.

Instead of ensuring that most of the primers participated in the reaction, all of the labelled unreacted primers could be removed from the system by, for example, using a potent 3' to 5' single-strand DNA exonuclease activity such as that of T4 DNA polymerase. By this approach, T4 DNA polymerase is added to the mixture after completion of the reaction with the exonuclease/polymerase of the invention. After a sufficient time of incubation, the label will be removed from the end of unreacted single-stranded primers, but little or none of the label will be removed from any extended reacted primers.

Another approach for eliminating unreacted, labeled primers as a potential source of unwanted background is to provide modified nucleoside triphosphates for incorporation into the extension product, which triphosphates when incorporated into this extension product facilitate separation of the exterior product from unreacted primer. For example, the nucleoside triphosphates may be modified with biotin, and then this biotinylated extension product could readily be indentified and/or separated from unreacted primer. Alternatively, the extension product could be treated with a backstrand primer including a tail, the backstrand primer capable of hybridizing with the extension product. The resulting double stranded DNA then could be separated from unreacted, labeled primer via the tail, and the presence or absence of label or the extension product determined.

It should also be clear to one skilled in the art that, prior to applying labeled extension product to a substrate carrying a complementary oligonucleotide, the extension product could be amplified by, for example, PCR. PCR is described in U.S. Pat. No. 4,683,195, the disclosure of which is incorporated herein by reference. Such a PCR amplification would be accomplished using a polymerase/exonuclease instead of the typical Taq polymerase which lacks 3' to 5' exonucleolytic activity. Also, such a PCR amplification would be accomplished using as a first primer, the labeled primer of the invention, and as a second primer, a typical primer complementary to a region "downstream" from the first primer. Preferably these primers are 20 nucleotides long and most preferably are 30 nucleotides long. This length will insure specific hybridization at the desired locations.

Another embodiment of this invention utilizes the detection of the free label which is removed from the primers in the case of a mismatch between the primer and the test DNA, instead of detecting the labelled nucleotide on an extension product. In this case, free label may be separated from the larger primers and test DNA by, for example, gel filtration on small columns of SEPHADEX G-25, a crosslinked polysaccharide (dextran) (Cat. No. 100 400, Boehringer-Mannheim Biochemicals, Indianapolis, Ind.). Primers and test DNA larger than about 15 nucleotides will be excluded in the void volume, while the free label will elute in the included volume. As would be understood by one skilled in the art, unreacted primers do not interfere with the test carried out in this way, and this method is also compatible with amplification of the signal by use of PCR as described above. In this embodiment, since the detection method is not based on extension product, it is not necessary that the exonucleolytic agent of the invention be associated with polymerase activity.

The products and methods of the invention may be used advantageously to determine allelic variation in genotyping studies. For example, if allelic variation is due to a single nucleotide substitution (or is correlated with such a substitution), then test DNA can be treated using primers to both alleles to determine whether an individual is homozygous or heterozygous with respect to those alleles. By use of the primers with unique tails described in the second embodiment of this invention, it is possible to test for all of the alleles of a single locus or even all of the alleles of several loci in a single reaction.

In selecting the primer, it is important that the presence or absence of a match at the test nucleotide determine whether label is excised or not. It is not necessary that the primer terminate at the position complementary with the test nucleotide. The primer also may include and terminate at a position close to the position complementary with the test nucleotide. For example, the position on the primer complementary with the test nucleotide may be the penultimate position. In this instance, a match at the penultimate position still must permit retention of label, and a mismatch at the penultimate position must be sufficient to cause excision of the label. Preferably, the primer terminates at or within four nucleotides of the position complementary to the test nucleotide.

It is not intended that the invention be limited to a exonucleolytic agent having a particular modification, but rather it is intended that the invention include any exonucleolytic agent having the capacity to retain a labeled nucleotide of a paired primer-DNA strand when there is a match and hybridization to the test nucleotide, and the capacity to remove a labeled nucleotide when there is no match or hybridization to the test nucleotide. Such an exonucleolytic agent may be of a mutant variety or may be a substantially pure preparation of an existing agent having the desired qualities.

It further should be understood that the method of the invention does not require a special exonucleolytic agent. It is important only that a primer be selected and paired with a DNA strand, and that conditions be applied such that label is retained if there is a match at the test nucleotide, and label is lost if there is a base-pair mismatch at the test nucleotide. Thus, rather than simply providing a particular primer or a particular exonucleolytic agent, the invention provides a system for determining the presence or absence of a test nucleotide at a particular position on a strand of DNA.

The invention may be employed to detect allelic variation or polymorphism due to a single base substitution on a strand of DNA. Such single nucleotide variation is known to be responsible for particular disease states, including beta-thalassemia, hemophilia, sickle cell anemia, and familial type III hypercholesterolemia. Such nucleotide variation also is known to be responsible for polymorphism, including polymorphism known to exist as restriction fragment length polymorphism (RFLP) (Lench, Stanier, & Williamson, 1988, *The Lancet*, June 18, pp. 1356–1358).

While the foregoing examples have been described in connection with polymorphism due to single nucleotide variation, it should be readily understood that the principles apply to deletions and other genomic variations as well.

EXAMPLE 1

Assay of a Specific Test Nucleotide in a Plasmid Sequence

The following assay detects the retention or loss of a labeled nucleotide at the 3' end of a primer following hybridization of the primer to a template test DNA and incubation with the polymerase/exonuclease. A polymerase/exonuclease suitable for practice of this invention will remove the labeled nucleotide when the oligonucleotide contains a mismatch at the terminal 3' position, but will retain the labeled nucleotide when the primer contains a match at the 3' position relative to the hybridizing sequence. The key feature of a polymerase/exonuclease is its ability to discriminate between a mismatch vs. match between the primer and the template, and to produce an extension product retaining the labeled nucleotide only if the latter situation obtains.

Figure 9:
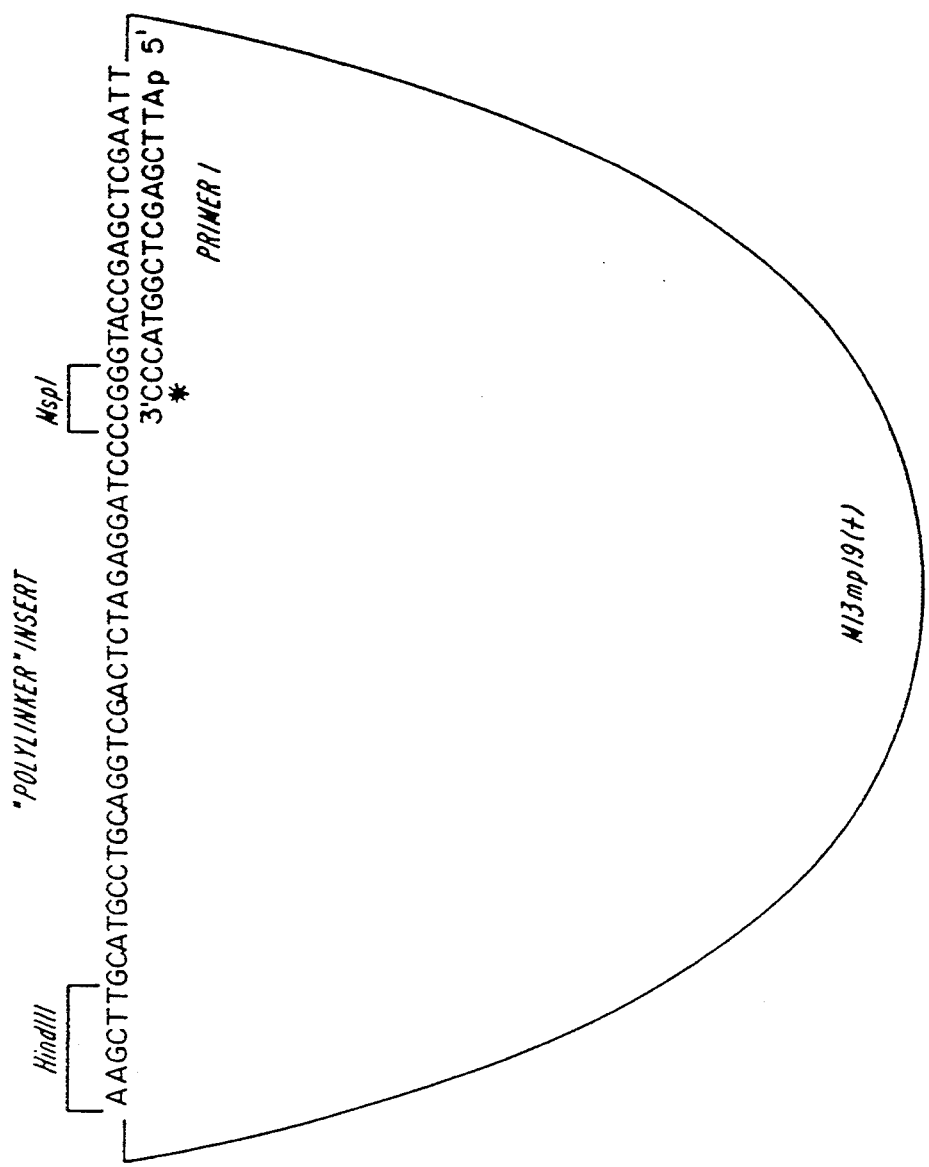
FIG. 9 schematically shows a primer of the invention hybridized to phage M13mp19(+) strand carrying a region complementary to the primer.

Two different 17 base pair primers are used to test for retention or loss of a labeled nucleotide using a template consisting of M13mp19 viral (+) strand carrying a "polylinker" insert (FIG. 9) (Yanisch-Perron et al., 1985, Gene 33: 103–119). A precursor of the desired primers and two different complements are obtained from Operon Technologies (San Pablo, Calif.) and have the following DNA sequences:

| Preprimer = | 5'ATTCGAGCTCGGTACC3' |
| complement 1 = | 5'GGGTACCGAGCTCGAATTCACTGGCCGTC3' |
| complement 2 = | 5'CGGTACCGAGCTCGAATTCACTGGCCGTC3' |

The preprimer is used in conjunction with each of the two 29-mer complements and $^{32}$P-dCTP (NEN/DuPont Research Products, Boston, Mass.) or $^{32}$P-dGTP (NEN/DuPont Research Products, supra) in a polymerase extension reaction with DNA polymerase I (Klenow fragment) (US Biochemical Corporation, Cleveland, Ohio) to produce the following two primers having $^{32}$P-labeled 3' terminal nucleotides:

| primer 1 = | 5'ATTCGAGCTCGGTACCC*3' |
| primer 2 = | 5'ATTCGAGCTCGGTACCG*3' |

Primer 1 is perfectly complementary to the M13mp19 template and after hybridization to (+) single-stranded M13mp19 it terminates with a $^{32}$P-labled "C" residue in the middle of an MspI (5'CCGG3') restriction site. Primer 2 differs from primer 1 at the 3' terminal $^{32}$P-labeled nucleotide to produce a G:G mismatch upon hybridization to the template. Since many randomly isolated RFLP probes detect polymorphisms at MspI restriction sites (Donis-Keller et al., 1987, Cell 51: 319–337), this primer-template set mimics a typical situation which occurs naturally at many human loci and which could be determined by the test of this invention.

The labeled primers are removed from their complementary templates by heat denaturation, and they are isolated from their longer templates and from unincorporated $^{32}$P-dNTPs by size separation using electrophoresis on a 20% polyacrylamide gel according to Maniatis, Fritsch, & Sambrook (1982, Molecular Cloning—A Laboratory Manual, Cold Spring Harbor Laboratory, Cold Spring Harbor, N.Y., pp. 173–177). Exposure of the gel to x-ray film reveals the location of the desired labeled 17-mer primers. That portion of the gel is cut out, and the DNA is eluted by following the procedure of Maniatis et al. (1982, supra, p. 178). The primers are precipitated twice with 3 volumes of ethanol and 1/10 volume of 3M NaOAc. The precipitated labeled primers are redissolved in 20 ul of TE buffer (pH 7.9).

The template is prepared by incubating 2 ug of M13mp19 double-stranded replicative form DNA with HindIII (New England Biolabs, Beverly, Mass.) according to the conditions recommended by the supplier. Sufficient HindIII is used to obtain completely cut M13mp19 DNA according to electrophoretic analysis of a small portion on agarose gels stained with ethidium bromide. The HindIII reaction is stopped by extraction of the reaction mixture with phenol followed by precipitation of the DNA with ethanol. Finally, the overhanging 5'termini are filled-in by incubation of redissolved HindIII-cut M13mp19 RF DNA with DNA polymerase I (Klenow fragment) and all four dNTPs. This reaction is terminated by phenol extraction and ethanol precipitation of the DNA. The cut, filled-in DNA is redissolved in TE (pH 7.9) buffer.

In two separate 15 ul mixtures, each primer (100 nM) is combined with 1 ug (about 0.2 pmole) of HindIII-cut and filled-in double-stranded M13mp19 replicative form vital DNA in a buffer consisting of 50 mM potassium phosphate (pH 7.5) and 6.6 mM $MgCl_2$. The mixtures are heated to 95° C. for 2 min. and cooled to 0° C. for 2 min. Next, all four dNTPs are added at 10 uM each and dithiothreitol is added to 2 mM to yield a final volume of 20 ul, and the mixtures are incubated at 37° C. for 5 min. Finally, 1 unit of DNA polymerase I (klenow fragment) (US Biochemicals, supra) is added to each mixture, and the "run-off" polymerization reactions are incubated for 5 min at 37° C.

The reactions are stopped by extraction with 20 ul of phenol followed by ethanol precipitation of the DNA. The DNA is redissolved in a buffer consisting of 80% deionized formamide, 10 mM NaOH, 1 mM EDTA, 0.1% xylene cyanol, 0.1% bromphenol blue, heated to 90° C. for 1 min, quick chilled to 0° C., loaded immediately on a 15% polyacrylamide gel, and subjected to eletrophoresis according to the method of Maniatis et al. (1982, supra, pp. 174–177). After exposure to x-ray film, the presence of label in the "run-off" products, in the residual unreacted primers, and released label is measured by the presence or absence of bands on the film at the relevant position.

The results show that the 54-mer extension product polymerized onto primer 1 retains its $^{32}P$ label while that polymerized onto primer 2 loses its $^{32}P$ label. This indicates that the test nucleotide position contained a "G" residue, complementary to the "C" present at that position on primer 1 and non-complementary to the "G" present at that position on primer 2. The lane containing the reaction products from incubation with primer 2 also contains $^{32}P$ label at the position of free nucleotides, indicating that the labeled 3' mismatched nucleotide on primer 2 was excised prior to polymerization of an extension product. The lanes containing reaction products from incubation with primer 1 and with primer 2 both show a $^{32}P$ labeled 17-mer which represents residual excess unreacted primer.

Adjustment of the concentration of assay components such as dNTPs, divalent cations, buffer components, and salts may be needed for maximum discrimination of matched and mismatched 3'-OH termini.

EXAMPLE 2

An Assay for a Nucleotide Substitution in the Human Beta Globin Gene Causing Sickle Cell Anemia.

The assay uses the following 39-mer preprimer and 40-mer complements, which are purchased from Operon Technologies (San Pablo, Calif.).

| | |
|---|---|
| preprimer: | 5'TTCACCTTGCCCCACAGGGCAGTAACGGCAGACTTCTCC3' |
| complement 1: | 5'AGGAGAAGTCTGCCGTTACTGCCCTGTGGGGCAAGGTGAA3' |
| complement 2: | 5'TGGAGAAGTCTGCCGTTACTGCCCTGTGGGGCAAGGTGAA3' |

In separate reactions, each of the two complements are lengthened by addition of poly(dA) to the 3' ends through the action of calf thymus terminal deoxynucleotidyl transferase (#70033, US Biochemicals Corp, Cleveland, Ohio) and dATP following the procedure of Maniatis et al. (1982, *Molecular Cloning—A laboratory manual*, Cold Spring Harbor Laboratory, Cold Spring Harbor, N.Y., pp. 239–140).

The preprimer is used in conjunction with each of the two complements and biotinylated dUTP (Bio-11-dUTP, #NU-806, ENZO Diagnostics, Inc., supra) or biotinylated dATP (biotin-7-dATP, #9509SA, Bethesda Research Laboratory, Gaithersburg, Md.) in a polymerase extension reaction with DNA polymerase I (Klenow fragment) (US Biochemical Corporation, Cleveland, Ohio) to produce the following two primers having biotinylated 3' terminal nucleotides:

| | |
|---|---|
| primer 1: | 5'TTCACCTTGCCCCACAGGGCAGTAACGGCAGACTTCTCCU 3' |
| primer 2: | 5'TTCACCTTGCCCCACAGGGCAGTAACGGCAGACTTCTCCA 3'. |

Primer 1 is perfectly homologous to the normal beta globin allele but has a 3' terminal U:T mismatch with the sickle cell allele, and primer 2 is perfectly homologous with the sickle cell beta globin allele but has a 3' terminal A:A mismatch with the normal beta globin allele. These primers avoid the potential for cross hybridization with the delta globin gene (which is highly homologous to beta globin) because they hybridize to the beta globin gene at a region in which there are 5 nucleotide differences between the two genes.

The labeled primers are removed from their poly-dA-lengthened complementary templates by heat denaturation, and they are isolated from their templates as described in example 1 or by chromatography over oligo-dT-cellulose columns (#20002, Oligo(dT)-cellulose/-Type 2, Collaborative Research, Inc., Bedford, Mass.) according to the method of Desrosiers et al. (1975, *Biochemistry* 14: 4367–4374). The primers in the flow through are precipitated with 3 volumes of ethanol and 1/10 volume of 3M NaOAc. The precipitated labeled primers are redissolved in 20 ul of TE buffer (pH 7.9).

Separate reactions are carried out with each primer using conditions described in the assay reaction of Example 1 except that 10 ug of human DNA is used as the template and the temperature for primer annealing is 65° C. The human DNA is obtained from human cell line GM2340A which is homozygous for the sickle cell allele (Hbs/Hbs) and from normal human cell line GM6167 (both obtained from the NIGMS Human Genetic Mutant Cell Repository, Camden, N.J.) by the procedure of Bell et al. (1981, *Proc. Nat'l. Acad. Sci. USA* 78: 5759–5763).

Following the reaction, the presence or absence of the biotin label in the extension product is determined as follows. The two samples are denaturated by addition of 1/10 volume of 1M NaOH and incubation at room temperature for 5 min. Next, they are hybridized with the following 30-mer oligonucleotide ("detection oligo") which is itself first bound to four separate nylon membranes: 5'ACCTCAAACAGACACCATGGTGCACCTGAC 3'.

In order to bind this detection oligonucleotide to a nylon solid support without hindering its ability to hybridize to the extension product of the test reaction, the oligonucleotide is first treated with calf thymus terminal deoxynucleotidyl transferase and dGTP according to the procedure of Maniatis et al. (1982, supra, pp. 239–240). The resulting "detection oligo" containing a poly-dG tail is then bound to discrete spots on four separate nylon membranes by use of the dot-blot device (ZetaProbe) and procedure of BioRad (Richmond, Calif.). The "detection oligo" is homologous to the beta globin sequence that will be attached to the primer after it has been extended by the polymerase/exonuclease of the invention.

Nylon membrane number 1 is hybridized with the sample resulting from the reaction with primer 1 and GM2340A DNA, nylon membrane number 2 with the sample resulting from primer 1 and GM6167 DNA, nylon membrane number 3 with the sample resulting from primer 2 and GM2340A DNA, and nylon membrane number 4 with the sample resulting from primer 2 and GM6167 DNA. The hybridization reaction is carried out for 30 min at 60° C. in 5 ml of 1M NaCl, 0.1M Tris-Cl, pH 7.5, 1 mM EDTA, 10 ug/ml heparin, 100 ug/ml single-stranded sonicated salmon sperm DNA, and 0.1% sarcosyl after pretreatment of the membrane under the same conditions in the absence of the sample for 30 min. The membranes are then washed in 2X SSC followed by 0.2X SSC at 50° C. to remove non-hybridized components, and developed as follows.

In separate reactions, each hybridized nylon membrane is incubated with a streptavidin-alkaline phosphatase complex (DETEK I-alk, ENZO Diagnostics, Inc. New York, N.Y.) according to the recommendations of the manufacturer. The membranes are then washed and incubated with the alkaline phosphatase substrate 3-bromo-4-chloro-3-indolyl phosphate and chromogen nitroblue tetrazolium (both from ENZO Diagnostics, Inc., supra) according to the recommendations of the manufacturer.

In this example, the human DNA from the normal cell line GM6167 which homozygous for the normal beta globin gene gives a much stronger signal with primer 1 (membrane #2) than with primer 2 (membrane #4), and the DNA from the homozygous sickle cell disease cell line GM2340A gives a much stronger signal with primer 2 (membrane #3) than with primer 1 (membrane #1).

A much stronger signal generated with primer 1 than with primer 2 indicates two normal alleles in the human DNA tested. Alternatively, a much stronger signal generated with primer 2 than with primer 1 indicates the presence of two sickle cell alleles, and an equally strong signal generated from both primers indicates that the DNA sample is heterozygous for the two alleles. In this example, the human DNA from the normal cell line GM6167, known to be homozygous for the normal beta globin gene, gives a much stronger signal with primer 1 (membrane #2) than with primer 2 (membrane #4), and the DNA from the homozygous sickle cell disease cell line GM2340A give a more intense signal with primer 2 (membrane #3) than with primer 1 (membrane #1).

It is intended that all matter contained in the above description or shown in the accompanying drawings shall be interpreted in an illustrative and not limiting sense.

What we claim is:

1. A method for detecting the presence or absence of a first nucleotide, at a position within a strand of DNA in a sample, comprising:

forming an admixture of primer and said strand of DNA in said sample and imposing hybridization conditions on said primer and said DNA strand to form a hybridization product, said primer comprising a sequence of DNA which hybridizes with said strand of DNA adjacent said first nucleotide position and having a second nucleotide opposite said first nucleotide position, said second nucleotide associated with a label, said second nucleotide hybridizing to said first nucleotide in the event said second nucleotide is complementary to said first nucleotide and said second nucleotide not hybridizing to said first nucleotide in the event of said second nucleotide is not complementary;

applying an enzymatic exonucleolytic agent to the hybridization product under conditions in which said second nucleotide is preferentially excised to form a labeled nucleotide product in the event said second nucleotide is not hybridized to said first nucleotide; and monitoring said sample for the presence of label in association with at least one of said products or primers, which label associated with said nucleotide product in concentrations greater than background is indicative of the absence of said first nucleotide, and which label associated with said primer or hybridization product in concentrations greater than background is indicative of the presence of said first nucleotide.

2. A method as claimed in claim 1 wherein said enzymatic exonucleolytic agent is an exonuclease having no polymerase activity.

3. A method as claimed in claim 1 wherein said primer bas a tail that is non-complementary with the DNA strand.

4. A method as claimed in claim 1 further characterized by detecting whether excision has occurred by assaying for the presence or absence of excised label.

5. A method as claimed in claim 1 further characterized by detecting whether excision has occurred by determining the presence or absence of label on primer that participated in the reaction.

6. A method as claimed in claim 5 further comprising separating primer that has participated in the reaction from unreacted primer prior to determining the presence or absence of label on primer that has participated in the reaction.

7. A method as claimed in claim 5 further comprising excising label from all unreacted primer prior to determining the presence or absence of label on primer that has participated in the reaction.

8. A method as claimed in claim 5 wherein said primer has a tail that is non-complementary with the DNA strand and further characterized by determining whether excision has occurred by attaching to a substrate an oligonucleotide at least in part complementary to the tail, subjecting the substrate to conditions that would allow the tail of any primer that has hybridized to the DNA strand to hybridize to the complementary oligonucleotide on the substrate, and detecting whether the primer hybridized to the substrate is labeled.

9. A method as claimed in claim 1 further comprising applying conditions to the hybridization product that allow the construction of a extension product complementary to a second portion of the DNA strand, the primer-extension product including the label of the primer if there is a match between the first and second nucleotides, but not if there is a mismatch and further comprising detecting whether excision has occurred by detecting the presence or absence of excised label or labelled primer-extension product.

10. A method as claimed in claim 9 wherein the presence or absence of label on the primer-extension product is detected by applying the primer-extension product to a substrate carrying an oligonucleotide complementary to the extension product, subjecting the substrate to conditions allowing the extension product and the complementary oligonucleotide to hybridize, and then detecting whether any extension product hybridized to the complementary oligonucleotide on the substrate is labeled.

11. A method as claimed in claim 9 wherein said primer has a tail that is non-complementary with the DNA strand, attaching to a substrate an oligonucleotide at least in part complementary to the tail, subjecting the substrate to conditions that would allow the tail of the extension product to hybridize to the complementary oligonucleotide on the substrate, and detecting whether primer-extension product hybridized to the complementary oligonucleotide on the substrate is labeled.

12. A method as claimed in claim 11 further comprising detecting the presence or absence of a plurality of nucleotides on a plurality of DNA strands by, treating a preparation of the DNA strands with a plurality of different labeled primers, each of the labeled primers having a unique tail, attaching unique complementary oligonucleotides at distinct locations on the substrate, each of the unique complementary oligonucleotides being complementary to one and only one of the tails, subjecting the substrate to conditions that would allow any primer-extension product to hybridize via its unique tail to the unique complementary oligonucleotide attached to the substrate, and detecting whether any primer-extension product hybridized at each of the distinct locations is labeled.

13. A method for detecting the genotype of an individual, the genotype being defined at least in part by single nucleotide variation at specific locations on DNA comprising, treating single stranded DNA with a plurality of unique oligonucleotide primers, each of the primers capable of hybridizing with a portion of the DNA adjacent to one of the single nucleotides, each of the primers having two ends, one end being a tail unique to each primer and the other end including a nucleotide at a position opposite to said one of the single nucleotides when the primers and DNA are initially hybridized, each of said primers being labeled at said nucleotide and the treatment including conditions causing the primers to hybridize with the DNA, treating the hybridized primers-DNA with an enzymatic exonucleolytic agent under conditions such that the enzymatic exonucleolytic agent preferentially excises the label if there is a mismatch at any said one of said single nucleotides, applying the primers to a substrate spotted at distinct locations with unique complementary oligonucleotides, each of the complementary oligonucleotides being complementary to one and only one of the tails, subjecting the substrate to conditions that would allow the tail of any primer to hybridize to the complementary oligonucleotide on the substrate, and detecting whether the primers hybridized at the distinct locations are labeled as an indication of the genotype of an individual.

* * * * *